(12) United States Patent
Fan et al.

(10) Patent No.: US 7,786,294 B2
(45) Date of Patent: Aug. 31, 2010

(54) COMPOSITIONS AND METHODS FOR AMPLIFICATION AND CLONING OF NEAR FULL-LENGTH VIRAL GENOME SAMPLES

(75) Inventors: Xiaofeng Fan, St. Louis, MO (US); Adrian M. Di Bisceglie, Ladue, MO (US)

(73) Assignee: Saint Louis University, Saint Louis, MO (US)

(*) Notice: Subject to any disclaimer, the term of this patent is extended or adjusted under 35 U.S.C. 154(b) by 491 days.

(21) Appl. No.: 11/756,250

(22) Filed: May 31, 2007

(65) Prior Publication Data

US 2007/0299255 A1     Dec. 27, 2007

Related U.S. Application Data

(60) Provisional application No. 60/804,194, filed on Jun. 8, 2006.

(51) Int. Cl.
*C07H 21/00*     (2006.01)

(52) U.S. Cl. ............... 536/25.3; 536/25.31; 536/25.32; 536/25.33; 536/25.34

(58) Field of Classification Search .................. None
See application file for complete search history.

(56) References Cited

U.S. PATENT DOCUMENTS 6,020,130 A * 2/2000 Gold et al. ................. 435/6

OTHER PUBLICATIONS

Schaefer Analytical Biochemistry (1995), vol. 227, pp. 255-273.*

* cited by examiner

*Primary Examiner*—Patrick T Lewis
(74) *Attorney, Agent, or Firm*—Randolph Bretton; The Law Office of Randolph Bretton

(57) ABSTRACT

A method of producing a polydeoxyribonucleotide molecule by reverse transcriptase polymerase chain reaction wherein the polydeoxyribonucleotide molecule has a length of greater than 5,000 base-pairs is disclosed. The method involves combining two reverse transcriptases followed by two protocols of polymerase chain reaction. This method enable the amplification of large DNAs, such as viruses, from a sample while preserving genetic diversity of the large DNA.

6 Claims, 6 Drawing Sheets

Figure 3

```
#19-2     GTYTTGGSAG RTVAGLSGLF QQGAKQD        #23-c16    GTHVTGGITA RATLGVASLF SPGPSQN
#19-3     S.......... .......... ..D....       #23-c18    ..Y....T.. .....I.... IS.....
#19-4     S.......... .....I.... .......       #23-c21    E.Y.S..S.. .....FTRF. .A.AK..
#19-5     .......... .......... .......        #23-c4     E.Y.S..S.. .....FTRF. .A.AK..
#19-6     S.......... .......... .......       #23-c7     D.Y.S..S.. .....FTRF. .A.AK..
#19-7     S.......... .......... .......       #23-c9     E.Y.S..S.. .....FTRF. .A.AK..
#19-8     .......... .......... .......        #23-1      .......SV. YN.R.F.G.. .T..K..
#19-9     S...I..... .....I.... .......        #23-2      .......SV. YN.R.F.G.. .T..K..
#19-10    .......... ........S.. .......       #23-3      .......SV. YN.R.F.G.. .T..K..
#19-11    .......... ........S.. .......       #23-4      .......SV. YN.R.F.G.. .T..K..
#19-12    .......... .......... .......        #23-5      .......SV. YN.R.F.G.. .T..K..
                                                #23-6      .......SV. YN.R.F.G.. .T..K..
                                                #23-7      .......SV. YN.R.F.G.. .T..K..
                                                #23-8      ....P..SV. YN.R.F.G.. .T..K..
                                                #23-9      .......SV. YN.R.F.G.. .T..K..
                                                #23-10     .......SV. YN.R.F.G.. .T..K..
                                                #23-11     .......SV. YN.R.F.G.. .T..K..
                                                #23-12     .......SV. YN.R.F.G.. .T..K..

#LRP19-3  .......... .......... .......        #LRP23-1   E.R.S..S.. H.A..IT... .S.AK..
#LRP19-10 .......... .......... .......        #LRP23-12  E.R.S..S.. .....T.... .T.AK..
#LRP19-12 .......... .......... .......        #LRP23-4   E......T.. .....I..FL IR.....
#LRP19-13 .......... .......... .......        #LRP23-9   E......T.. .....I..FL IR.....
#LRP19-1  .......... .......... .......        #LRP23-7   E......T.. .....I..FL IR.....
#LRP19-4  .......... .......... .......        #LRP23-3   E......T.. .....I..FL IR.....
#LRP19-5  .......... .......... .......        #LRP23-8   E......T.. .....I..FL IR.....
#LRP19-6  S.......... .......... .......       #LRP23-6   E......T.. .....I..FL IR.....
#LRP19-14 S.......... .....I.... .K.....       #LRP23-2   ..Y....T.. .....I.... N......
#LRP19-11 S.......... .....I.... .......       #LRP23-11  ..Y....T.. .....I.... IS.....
#LRP19-8  S.......... .......... .......       #LRP23-14  ..Y....T.. .....I.... IS.....
#LRP19-2  S.......... .......... .......       #LRP23-15  ..Y....T.. .....I.... I......
#LRP19-9  S.......... .......... .......       #LRP23-5   E......SA. Q.AF.FS... IR.AR..
#LRP19-7  R.......... .......... .......       #LRP23-10  E......SA. Q.AF.FS... IR.AR..
#LRP19-15 R.......... .......... .......       #LRP23-13  E.YLS..S.. .....LTRF. .ARAKH.
#LRP19-16 S.......... ........S.. .......
```

A                                              B

Table 1

|  | Primer | Polarity | Sequence (5'-3') | Position | $T_m$(°C) |
|---|---|---|---|---|---|
| RT | QR1 | Anti-sense | Cggttggggaggaggtag | 9356-9373 | 60.5 |
|  | QR2 | Anti-sense | Tagccagccgtgaaccag | 9248-9265 | 61 |
|  | QR268 | Anti-sense | Gctgtagccagccgtgaaccag | 9248-9269 | 68.5 |
|  | QR274 | Anti-sense | Ccgctgtagccagccgtgaaccag | 9248-9271 | 74.4 |
|  | QR3* | Anti-sense | Cagccctgcctcctctgg | 9139-9156 | 64.5 |
|  | QR4 | Anti-sense | Ggttggggaggaggtagatg | 9353-9372 | 60.7 |
|  | QR5 | Anti-sense | Tgcagcaagcaggagtagg | 9326-9344 | 60.3 |
|  | QR6 | Anti-sense | Atcggttggggaggaggtag | 9356-9375 | 62.5 |
|  | QR7* | Anti-sense | Atcagtatcatcctcgcccac | 8858-8878 | 61.3 |
|  | Q5BR1 | Anti-sense | Gcagcaagcaggagtaggcaa | 9323-9343 | 65.1 |
|  | Q5BR2 | Anti-sense | Tatcggagtgagtttgagct | 9199-9218 | 55.1 |
|  | Q5BR3 | Anti-sense | Tttgagctttgttcttactg | 9187-9206 | 50.9 |
| PCR | QUF1 | Sense | Ggcgacactccaccatagatc | 18-38 | 61.8 |
|  | QUF2 | Sense | Gccgagtagtgttgggtc | 253-270 | 56.5 |
|  | QUF3 | Sense | Ctgtgaggaactactgtcttc | 45-65 | 51.5 |
|  | QUF4 | Sense | Ctgcctgatagggtgcttg | 289-307 | 59.4 |
|  | QUF5 | Sense | Actccctgtgaggaactac | 39-58 | 55.7 |
|  | WF1 | Sense | Actccctgtgaggaactactgtcttcac | 39-67 | 67.8 |
|  | WF2 | Sense | Actgtcttcacgcagaaagcgtctagc | 57-83 | 68.9 |
|  | WF3 | Sense | Agaaagcgtctagccatggcgttag | 70-94 | 67.6 |
|  | WF33 | Sense | Acgcagaaagcgtctagccat | 66-86 | 63.5 |
|  | WF4 | Sense | Tagtatgagtgtcgtgcagcctcca | 92-116 | 67.2 |
|  | WF5** | Sense | ggatctgacgttaattaacatagtggtctgcggaaccggt | 139-160 | 67.5 |
|  | WF6 | Sense | Gactgctagccgagtagtgttgggtc | 245-270 | 67.4 |
|  | WF7 | Sense | Tggtactgcctgatagggtgcttg | 284-307 | 66.5 |
|  | WR1* | Anti-sense | Ctattrattcacctggagagtaactgtggag | 9021-9052 | 67.6 |
|  | WR2* | Anti-sense | Ctgaggcatgcggccacc | 9053-9070 | 68.7 |
|  | WR3* | Anti-sense | Cggtgtctccaagctcgcaa | 9090-9109 | 67.1 |
|  | WR4* | Anti-sense | Agaaygctagcgcggacgctc | 9116-9136 | 65.5 |
|  | WR5 | Anti-sense | Gcagccctgcctcctctgg | 9139-9157 | 68.0 |
|  | WTR5 | Anti-sense | Gcagccctacctcctctgg | 9139-9157 | 62.3 |
|  | WR55** | Anti-sense | atagctgggtggccggccatggcagccctacctcctctgg | 9139-9160 | 67.9 |
|  | WR6 | Anti-sense | Ttggagtgagtttgagctttgttcttactg | 9187-9216 | 66.7 |
|  | WR7 | Anti-sense | Gccgctattggagtgagtttgagc | 9200-9223 | 67.3 |
|  | HCV6 | Anti-sense | Ggtaccccaagtttrctgaggca | 9063-9085 | 63.5 |
|  | HCV7 | Anti-sense | Gagtaactgtggagtgaaaaygcg | 9011-9034 | 62.2 |
| 5'UTR | QUF3 | Sense | Ctgtgaggaactactgtcttc | 45-65 | 257 bp |
|  | QUR3 | Anti-sense | Ccctatcaggcagtaccacaa | 281-301 |  |
| Core | CoreF2 | Sense | Tactgcctgatagggtgcttg | 287-307 | 709 bp |
|  | CoreR3 | Anti-sense | Atcggccgyctcgtacacaat | 975-995 |  |
| E1/E2 | QRAF2 | Sense | Aactgttcaccttctctccca | 1207-1227 | 496 bp |
|  | Q6AR1 | Anti-sense | Tcgggacagcctgaagagttg | 1682-1702 |  |
| NS3 | NS3AF2 | Sense | Tgtggagaacctagagacaac | 3933-3953 | 316 bp |
|  | NS3AR2 | Anti-sense | Cgtcggcaaggaacttgccrt | 4228-4248 |  |
| NS5A | Q5AF2 | Sense | Atccctcccatataacagcag | 6871-6891 | 251 bp |
|  | Q5AR2 | Antisense | Acaagcggatcgaaggagtcca | 7099-7121 |  |
| NS5B | Q5BF2 | Sense | Atccgtacggaggaggcaat | 8298-8317 | 921 bp |
|  | Q5BR2 | Anti-sense | Tatcggagtgagtttgagct | 9199-9218 |  |

Table 2

| Sample | Amplicon | Number of Clones | Genetic Complexity | | Genetic Distance | | |
|---|---|---|---|---|---|---|---|
| | | | Nucleotide | Amino Acid | d | ds | dn |
| LIV19 | 1.38 kb fragment | 11 | 0.770 | 0.685 | 0.026 | 0.022 | 0.028 |
| | 9.1 kb fragment (LRP) | 16 | 0.537* | 0.800* | 0.025* | 0.036* | 0.020* |
| LIV23 | 1.38 kb fragment | 18 | 0.430 | 0.430 | 0.164 | 0.098 | 0.197 |
| | 9.1 kb fragment (LRP) | 15 | 0.620* | 0.829** | 0.113* | 0.144* | 0.101* |

SEQUENCE LISTING

<160> NUMBER OF SEQ ID NOS: 69

<210> SEQ ID NO 1
<211> LENGTH: 27
<212> TYPE: PRT
<213> ORGANISM: Hepatitis C virus

<400> SEQUENCE: 1

Gly Thr Tyr Thr Thr Gly Gly Ser Ala Gly Arg Thr Val Ala Gly Leu
1               5                   10                  15

Ser Gly Leu Phe Gln Gln Gly Ala Lys Gln Asp
            20                  25

<210> SEQ ID NO 2
<211> LENGTH: 27
<212> TYPE: PRT
<213> ORGANISM: Hepatitis C virus

<400> SEQUENCE: 2

Ser Thr Tyr Thr Thr Gly Gly Ser Ala Gly Arg Thr Val Ala Gly Leu
1               5                   10                  15

Ser Gly Leu Phe Gln Gln Asp Ala Lys Gln Asp
            20                  25

<210> SEQ ID NO 3
<211> LENGTH: 27
<212> TYPE: PRT
<213> ORGANISM: Hepatitis C virus

<400> SEQUENCE: 3

Ser Thr Tyr Thr Thr Gly Gly Ser Ala Gly Arg Thr Val Ala Gly Ile
1               5                   10                  15

Ser Gly Leu Phe Gln Gln Gly Ala Lys Gln Asp
            20                  25

<210> SEQ ID NO 4
<211> LENGTH: 27
<212> TYPE: PRT
<213> ORGANISM: Hepatitis C virus

<400> SEQUENCE: 4

Ser Thr Tyr Thr Thr Gly Gly Ser Ala Gly Arg Thr Val Ala Gly Leu
1               5                   10                  15

Ser Gly Leu Phe Gln Gln Gly Ala Lys Gln Asp
            20                  25

<210> SEQ ID NO 5
<211> LENGTH: 27
<212> TYPE: PRT
<213> ORGANISM: Hepatitis C virus

<400> SEQUENCE: 5

Ser Thr Tyr Thr Ile Gly Gly Ser Ala Gly Arg Thr Val Ala Gly Ile
1               5                   10                  15

Ser Gly Leu Phe Gln Gln Gly Ala Lys Gln Asp
            20                  25

<210> SEQ ID NO 6
<211> LENGTH: 27
<212> TYPE: PRT
<213> ORGANISM: Hepatitis C virus -continued

```
<400> SEQUENCE: 6

Gly Thr Tyr Thr Thr Gly Gly Ser Ala Gly Arg Thr Val Ala Gly Leu
1               5                   10                  15

Ser Ser Leu Phe Gln Gln Gly Ala Lys Gln Asp
            20                  25

<210> SEQ ID NO 7
<211> LENGTH: 27
<212> TYPE: PRT
<213> ORGANISM: Hepatitis C virus

<400> SEQUENCE: 7

Ser Thr Tyr Thr Thr Gly Gly Ser Ala Gly Arg Thr Val Ala Gly Ile
1               5                   10                  15

Ser Gly Leu Phe Gln Lys Gly Ala Lys Gln Asp
            20                  25

<210> SEQ ID NO 8
<211> LENGTH: 27
<212> TYPE: PRT
<213> ORGANISM: Hepatitis C virus

<400> SEQUENCE: 8

Arg Thr Tyr Thr Thr Gly Gly Ser Ala Gly Arg Thr Val Ala Gly Leu
1               5                   10                  15

Ser Gly Leu Phe Gln Gln Gly Ala Lys Gln Asp
            20                  25

<210> SEQ ID NO 9
<211> LENGTH: 27
<212> TYPE: PRT
<213> ORGANISM: Hepatitis C virus

<400> SEQUENCE: 9

Ser Thr Tyr Thr Thr Gly Gly Ser Ala Gly Arg Thr Val Ala Gly Leu
1               5                   10                  15

Ser Ser Leu Phe Gln Gln Gly Ala Lys Gln Asp
            20                  25

<210> SEQ ID NO 10
<211> LENGTH: 27
<212> TYPE: PRT
<213> ORGANISM: Hepatitis C virus

<400> SEQUENCE: 10

Gly Thr His Val Thr Gly Gly Ile Thr Ala Arg Ala Thr Leu Gly Val
1               5                   10                  15

Ala Ser Leu Phe Ser Pro Gly Pro Ser Gln Asn
            20                  25

<210> SEQ ID NO 11
<211> LENGTH: 27
<212> TYPE: PRT
<213> ORGANISM: Hepatitis C virus

<400> SEQUENCE: 11

Gly Thr Tyr Val Thr Gly Gly Thr Ala Arg Ala Thr Leu Gly Ile
1               5                   10                  15

Ala Ser Leu Phe Thr Ser Gly Pro Ser Gln Asn
            20                  25
```

```
<210> SEQ ID NO 12
<211> LENGTH: 27
<212> TYPE: PRT
<213> ORGANISM: Hepatitis C virus

<400> SEQUENCE: 12

Glu Thr Tyr Val Ser Gly Gly Ser Thr Ala Arg Ala Thr Leu Gly Phe
1               5                   10                  15

Thr Arg Phe Phe Ser Ala Gly Ala Lys Gln Asn
            20                  25

<210> SEQ ID NO 13
<211> LENGTH: 27
<212> TYPE: PRT
<213> ORGANISM: Hepatitis C virus

<400> SEQUENCE: 13

Asp Thr Tyr Val Ser Gly Gly Ser Thr Ala Arg Ala Thr Leu Gly Phe
1               5                   10                  15

Thr Arg Phe Phe Ser Ala Gly Ala Lys Gln Asn
            20                  25

<210> SEQ ID NO 14
<211> LENGTH: 27
<212> TYPE: PRT
<213> ORGANISM: Hepatitis C virus

<400> SEQUENCE: 14

Gly Thr His Val Thr Gly Gly Ser Val Ala Tyr Asn Thr Arg Gly Phe
1               5                   10                  15

Ala Gly Leu Phe Ser Thr Gly Pro Lys Gln Asn
            20                  25

<210> SEQ ID NO 15
<211> LENGTH: 27
<212> TYPE: PRT
<213> ORGANISM: Hepatitis C virus

<400> SEQUENCE: 15

Gly Thr His Val Pro Gly Gly Ser Val Ala Tyr Asn Thr Arg Gly Phe
1               5                   10                  15

Ala Gly Leu Phe Ser Thr Gly Pro Lys Gln Asn
            20                  25

<210> SEQ ID NO 16
<211> LENGTH: 27
<212> TYPE: PRT
<213> ORGANISM: Hepatitis C virus

<400> SEQUENCE: 16

Glu Thr Arg Val Ser Gly Gly Ser Thr Ala His Ala Ala Leu Gly Ile
1               5                   10                  15

Thr Ser Leu Phe Ser Ser Gly Ala Lys Gln Asn
            20                  25

<210> SEQ ID NO 17
<211> LENGTH: 27
<212> TYPE: PRT
<213> ORGANISM: Hepatitis C virus

<400> SEQUENCE: 17

Glu Thr Arg Val Ser Gly Gly Ser Thr Ala Arg Ala Thr Leu Gly Val
```

```
                 1               5                  10                 15
Thr Ser Leu Phe Ser Thr Gly Ala Lys Gln Asn
            20                  25

<210> SEQ ID NO 18
<211> LENGTH: 27
<212> TYPE: PRT
<213> ORGANISM: Hepatitis C virus

<400> SEQUENCE: 18

Glu Thr His Val Thr Gly Gly Thr Thr Ala Arg Ala Thr Leu Gly Ile
1               5                  10                  15

Ala Ser Phe Leu Thr Arg Gly Pro Ser Gln Asn
            20                  25

<210> SEQ ID NO 19
<211> LENGTH: 27
<212> TYPE: PRT
<213> ORGANISM: Hepatitis C virus

<400> SEQUENCE: 19

Gly Thr Tyr Val Thr Gly Gly Thr Thr Ala Arg Ala Thr Leu Gly Ile
1               5                  10                  15

Ala Ser Leu Phe Asn Pro Gly Pro Ser Gln Asn
            20                  25

<210> SEQ ID NO 20
<211> LENGTH: 27
<212> TYPE: PRT
<213> ORGANISM: Hepatitis C virus

<400> SEQUENCE: 20

Gly Thr Tyr Val Thr Gly Gly Thr Thr Ala Arg Ala Thr Leu Gly Ile
1               5                  10                  15

Ala Ser Leu Phe Thr Ser Gly Pro Ser Gln Asn
            20                  25

<210> SEQ ID NO 21
<211> LENGTH: 27
<212> TYPE: PRT
<213> ORGANISM: Hepatitis C virus

<400> SEQUENCE: 21

Gly Thr Tyr Val Thr Gly Gly Thr Thr Ala Arg Ala Thr Leu Gly Ile
1               5                  10                  15

Ala Ser Leu Phe Thr Pro Gly Pro Ser Gln Asn
            20                  25

<210> SEQ ID NO 22
<211> LENGTH: 27
<212> TYPE: PRT
<213> ORGANISM: Hepatitis C virus

<400> SEQUENCE: 22

Glu Thr His Val Thr Gly Gly Ser Ala Ala Gln Ala Ala Phe Gly Phe
1               5                  10                  15

Ser Ser Leu Phe Thr Arg Gly Ala Arg Gln Asn
            20                  25

<210> SEQ ID NO 23
<211> LENGTH: 27
<212> TYPE: PRT
```

<213> ORGANISM: Hepatitis C virus

<400> SEQUENCE: 23

Glu Thr Tyr Leu Ser Gly Gly Ser Thr Ala Arg Ala Thr Leu Gly Leu
1               5                   10                  15

Thr Arg Phe Phe Ser Ala Arg Ala Lys His Asn
            20                  25

<210> SEQ ID NO 24
<211> LENGTH: 18
<212> TYPE: DNA
<213> ORGANISM: Hepatitis C virus

<400> SEQUENCE: 24
cggttgggga ggaggtag                                                 18

<210> SEQ ID NO 25
<211> LENGTH: 18
<212> TYPE: DNA
<213> ORGANISM: Hepatitis C virus

<400> SEQUENCE: 25
tagccagccg tgaaccag                                                 18

<210> SEQ ID NO 26
<211> LENGTH: 22
<212> TYPE: DNA
<213> ORGANISM: Hepatitis C virus

<400> SEQUENCE: 26
gctgtagcca gccgtgaacc ag                                            22

<210> SEQ ID NO 27
<211> LENGTH: 24
<212> TYPE: DNA
<213> ORGANISM: Hepatitis C virus

<400> SEQUENCE: 27
ccgctgtagc cagccgtgaa ccag                                          24

<210> SEQ ID NO 28
<211> LENGTH: 18
<212> TYPE: DNA
<213> ORGANISM: Hepatitis C virus

<400> SEQUENCE: 28
cagccctgcc tcctctgg                                                 18

<210> SEQ ID NO 29
<211> LENGTH: 20
<212> TYPE: DNA
<213> ORGANISM: Hepatitis C virus

<400> SEQUENCE: 29
ggttggggag gaggtagatg                                               20

<210> SEQ ID NO 30
<211> LENGTH: 19
<212> TYPE: DNA
<213> ORGANISM: Hepatitis C virus

<400> SEQUENCE: 30
tgcagcaagc aggagtagg                                                19

<210> SEQ ID NO 31
<211> LENGTH: 20
<212> TYPE: DNA
<213> ORGANISM: Hepatitis C virus

<400> SEQUENCE: 31
atcggttggg gaggaggtag                                               20

<210> SEQ ID NO 32
<211> LENGTH: 21
<212> TYPE: DNA
<213> ORGANISM: Hepatitis C virus

<400> SEQUENCE: 32
atcagtatca tcctcgccca c                                             21

<210> SEQ ID NO 33
<211> LENGTH: 21
<212> TYPE: DNA
<213> ORGANISM: Hepatitis C virus

<400> SEQUENCE: 33
gcagcaagca ggagtaggca a                                             21

<210> SEQ ID NO 34
<211> LENGTH: 20
<212> TYPE: DNA
<213> ORGANISM: Hepatitis C virus

<400> SEQUENCE: 34
tatcggagtg agtttgagct                                               20

<210> SEQ ID NO 35
<211> LENGTH: 20
<212> TYPE: DNA
<213> ORGANISM: Hepatitis C virus

<400> SEQUENCE: 35
tttgagcttt gttcttactg                                               20

<210> SEQ ID NO 36
<211> LENGTH: 21
<212> TYPE: DNA
<213> ORGANISM: Hepatitis C virus

<400> SEQUENCE: 36
ggcgacactc caccatagat c                                             21

<210> SEQ ID NO 37
<211> LENGTH: 18
<212> TYPE: DNA
<213> ORGANISM: Hepatitis C virus

<400> SEQUENCE: 37
gccgagtagt gttgggtc                                                 18

<210> SEQ ID NO 38
<211> LENGTH: 21
<212> TYPE: DNA
<213> ORGANISM: Hepatitis C virus

<400> SEQUENCE: 38

```
ctgtgaggaa ctactgtctt c                                          21

<210> SEQ ID NO 39
<211> LENGTH: 19
<212> TYPE: DNA
<213> ORGANISM: Hepatitis C virus

<400> SEQUENCE: 39
ctgcctgata gggtgcttg                                             19

<210> SEQ ID NO 40
<211> LENGTH: 20
<212> TYPE: DNA
<213> ORGANISM: Hepatitis C virus

<400> SEQUENCE: 40
actcccctgt gaggaactac                                            20

<210> SEQ ID NO 41
<211> LENGTH: 29
<212> TYPE: DNA
<213> ORGANISM: Hepatitis C virus

<400> SEQUENCE: 41
actcccctgt gaggaactac tgtcttcac                                  29

<210> SEQ ID NO 42
<211> LENGTH: 27
<212> TYPE: DNA
<213> ORGANISM: Hepatitis C virus

<400> SEQUENCE: 42
actgtcttca cgcagaaagc gtctagc                                    27

<210> SEQ ID NO 43
<211> LENGTH: 25
<212> TYPE: DNA
<213> ORGANISM: Hepatitis C virus

<400> SEQUENCE: 43
agaaagcgtc tagccatggc gttag                                      25

<210> SEQ ID NO 44
<211> LENGTH: 21
<212> TYPE: DNA
<213> ORGANISM: Hepatitis C virus

<400> SEQUENCE: 44
acgcagaaag cgtctagcca t                                          21

<210> SEQ ID NO 45
<211> LENGTH: 25
<212> TYPE: DNA
<213> ORGANISM: Hepatitis C virus

<400> SEQUENCE: 45
tagtatgagt gtcgtgcagc ctcca                                      25

<210> SEQ ID NO 46
<211> LENGTH: 40
<212> TYPE: DNA
<213> ORGANISM: Hepatitis C virus

<400> SEQUENCE: 46
```

```
ggatctgacg ttaattaaca tagtggtctg cggaaccggt                    40

<210> SEQ ID NO 47
<211> LENGTH: 26
<212> TYPE: DNA
<213> ORGANISM: Hepatitis C virus

<400> SEQUENCE: 47
gactgctagc cgagtagtgt tgggtc                                  26

<210> SEQ ID NO 48
<211> LENGTH: 24
<212> TYPE: DNA
<213> ORGANISM: Hepatitis C virus

<400> SEQUENCE: 48
tggtactgcc tgatagggtg cttg                                    24

<210> SEQ ID NO 49
<211> LENGTH: 32
<212> TYPE: DNA
<213> ORGANISM: Hepatitis C virus

<400> SEQUENCE: 49
ctattrattt cacctggaga gtaactgtgg ag                           32

<210> SEQ ID NO 50
<211> LENGTH: 18
<212> TYPE: DNA
<213> ORGANISM: Hepatitis C virus

<400> SEQUENCE: 50
ctgaggcatg cggccacc                                           18

<210> SEQ ID NO 51
<211> LENGTH: 20
<212> TYPE: DNA
<213> ORGANISM: Hepatitis C virus

<400> SEQUENCE: 51
cggtgtctcc aagctcgcaa                                         20

<210> SEQ ID NO 52
<211> LENGTH: 21
<212> TYPE: DNA
<213> ORGANISM: Hepatitis C virus

<400> SEQUENCE: 52
agaagyctag cgcggacgct c                                       21

<210> SEQ ID NO 53
<211> LENGTH: 19
<212> TYPE: DNA
<213> ORGANISM: Hepatitis C virus

<400> SEQUENCE: 53
gcagccctgc ctcctctgg                                          19

<210> SEQ ID NO 54
<211> LENGTH: 19
<212> TYPE: DNA
<213> ORGANISM: Hepatitis C virus
```

```
<400> SEQUENCE: 54
gcagccctac ctcctctgg                                                    19

<210> SEQ ID NO 55
<211> LENGTH: 40
<212> TYPE: DNA
<213> ORGANISM: Hepatitis C virus

<400> SEQUENCE: 55
atagctgggt ggccggccat ggcagcccta cctcctctgg                             40

<210> SEQ ID NO 56
<211> LENGTH: 30
<212> TYPE: DNA
<213> ORGANISM: Hepatitis C virus

<400> SEQUENCE: 56
ttggagtgag tttgagcttt gttcttactg                                        30

<210> SEQ ID NO 57
<211> LENGTH: 24
<212> TYPE: DNA
<213> ORGANISM: Hepatitis C virus

<400> SEQUENCE: 57
gccgctattg gagtgagttt gagc                                              24

<210> SEQ ID NO 58
<211> LENGTH: 23
<212> TYPE: DNA
<213> ORGANISM: Hepatitis C virus

<400> SEQUENCE: 58
ggtaccccaa gtttrctgag gca                                               23

<210> SEQ ID NO 59
<211> LENGTH: 24
<212> TYPE: DNA
<213> ORGANISM: Hepatitis C virus

<400> SEQUENCE: 59
gagtaactgt ggagtgaaaa ygcg                                              24

<210> SEQ ID NO 60
<211> LENGTH: 21
<212> TYPE: DNA
<213> ORGANISM: Hepatitis C virus

<400> SEQUENCE: 60
ccctatcagg cagtaccaca a                                                 21

<210> SEQ ID NO 61
<211> LENGTH: 21
<212> TYPE: DNA
<213> ORGANISM: Hepatitis C virus

<400> SEQUENCE: 61
tactgcctga tagggtgctt g                                                 21

<210> SEQ ID NO 62
<211> LENGTH: 21
<212> TYPE: DNA
<213> ORGANISM: Hepatitis C virus
```

-continued

```
<400> SEQUENCE: 62
atcggccgyc tcgtacacaa t                                              21

<210> SEQ ID NO 63
<211> LENGTH: 21
<212> TYPE: DNA
<213> ORGANISM: Hepatitis C virus

<400> SEQUENCE: 63
aactgttcac cttctctccc a                                              21

<210> SEQ ID NO 64
<211> LENGTH: 21
<212> TYPE: DNA
<213> ORGANISM: Hepatitis C virus

<400> SEQUENCE: 64
tcgggacagc ctgaagagtt g                                              21

<210> SEQ ID NO 65
<211> LENGTH: 21
<212> TYPE: DNA
<213> ORGANISM: Hepatitis C virus

<400> SEQUENCE: 65
tgtggagaac ctagagacaa c                                              21

<210> SEQ ID NO 66
<211> LENGTH: 21
<212> TYPE: DNA
<213> ORGANISM: Hepatitis C virus

<400> SEQUENCE: 66
cgtcggcaag gaacttgccr t                                              21

<210> SEQ ID NO 67
<211> LENGTH: 21
<212> TYPE: DNA
<213> ORGANISM: Hepatitis C virus

<400> SEQUENCE: 67
atccctccca tataacagca g                                              21

<210> SEQ ID NO 68
<211> LENGTH: 22
<212> TYPE: DNA
<213> ORGANISM: Hepatitis C virus

<400> SEQUENCE: 68
acaagcggat cgaaggagtc ca                                             22

<210> SEQ ID NO 69
<211> LENGTH: 20
<212> TYPE: DNA
<213> ORGANISM: Hepatitis C virus

<400> SEQUENCE: 69
atccgtacgg aggaggcaat                                                20
```

US 7,786,294 B2

COMPOSITIONS AND METHODS FOR AMPLIFICATION AND CLONING OF NEAR FULL-LENGTH VIRAL GENOME SAMPLES

PATENT CASE TEXT

This application for patent claims priority to U.S. provisional patent application No. 60/804,194, which was filed 8 Jun. 2006.

BACKGROUND OF THE INVENTION

1. Field of the Invention

This invention relates generally to compositions and methods of amplifying and cloning nucleic acid sequences. Specifically, the invention is directed to compositions and methods using reverse transcriptase, polymerase chain reaction, and cloning vectors for the production of full length nucleic acid sequences from viral genomes.

2. Description of the Related Art

Long RT-PCR (LRP) amplification of RNA templates is sometimes difficult compared to long PCR of DNA templates. There exists a long felt need for a reliable method of replicating and amplifying sequences from long RNA templates. Polymerase chain reaction (PCR) is an indispensable technique in biomedical research. With known primer sequences, it can easily amplify a DNA target less than 3 kb but it has diminished power when the target is larger than 3 kb. In 1994, Barnes et al first hypothesized that the inability to amplify large DNA fragments was due to the misincorporation of nucleotides by most thermostable DNA polymerases, which resulted in premature termination of PCR [1]. Based on this hypothesis, mixed polymerases, one of which has 3' to 5' exonuclease "proofreading" activity to correct the misincorporation, have successfully amplified DNA targets up to 42 kb [2]. However, there has been limited success in applying this concept to the amplification of large RNA genomes that require the reverse transcription (RT) step prior to PCR amplification. Compared to the amplification of DNA targets, it is reasonable to hypothesize that the RT step is of crucial importance during long RT-PCR (LRP) performance when taking into account the following characteristics. First, in most situations, the solution buffers are not compatible between RT and PCR. Only part of the RT reaction can be used for subsequent PCR and thus reduces the sensitivity dramatically. Second, most RT enzymes have an inhibitory role for thermostable DNA polymerases [3]. Third, RT is conducted at temperatures ranging from 37° C. to 50° C. at which the RNA template may retain its secondary structure that makes RT stop prematurely. Such situations are even more challenging when trying to amplify full-length hepatitis C virus (HCV) genome, a positive sense single-strand RNA virus in the family of flavirividae. There is extensive secondary structure along the entire HCV genome [4-6]. Furthermore, HCV cannot be cultured in vitro. The only source of RNA template for LRP is clinical samples in which HCV has a low titer.

The inventors have sought to investigate each step of the LRP procedure and developed a robust protocol for the efficient amplification and cloning of near full-length HCV genome from clinical samples, and in addition estimate the sensitivity and potential PCR-mediated recombination related to this protocol.

SUMMARY OF THE INVENTION

The Inventors have created a comprehensive optimization protocol that allows robust amplification of a 9.1 kb fragment of HCV, followed by efficient cloning into a novel vector. Among RNA templates, hepatitis C virus (HCV) represents an excellent example to challenge the potential of LRP technology due to its extensive secondary structures and its difficulty to be readily cultured in vitro. The only source for viral genome amplification is clinical samples in which HCV is usually present at low titers. Detailed analyses indicate the lack of potential LRP-mediated recombination and the preservation of viral diversity. Thus, the invention could be applied for the amplification of other difficult RNA templates and may facilitate RNA virus research such as linked viral mutations and reverse genetics.

In one embodiment, methods and compositions for LRP may be packaged as a kit in order to facilitate the accurate and efficient production of DNA form long target RNA templates such as full length retroviral genomes.

In another embodiment methods and compositions of each stage of LRP may be packaged separately such as the stages of RNA extraction, reverse transcriptase, PCR, and cloning, in order to enable the researcher to customize the LRP protocol to their specific research needs.

BRIEF DESCRIPTION OF THE DRAWINGS

FIG. 3: Comparison of HCV HVR1 (27 aa) quasispecies profiles derived from either 1.38 kb or 9.1 kb amplicons. Dots indicate the identity to the top line of amino acid sequence. While there is no obvious difference for sample LIV19 (A), LIV23 displays much distinct HVR1 quasispecies profiles from two sizes of amplicons, 1.38 kb and 9.1 kb, respectively. Sequences may be identified in the Sequence Listing as follows: #19-2 (SEQ ID NO: 1); #19-3 (SEQ ID NO: 2); #19-4 (SEQ ID NO: 3); #19-5 (SEQ ID NO: 1); #19-6 (SEQ ID NO: 4); #19-7 (SEQ ID NO: 4); #19-8 (SEQ ID NO: 1); #19-9 (SEQ ID NO: 5); #19-10 (SEQ ID NO: 6); #19-11 (SEQ ID NO: 6); #19-12 (SEQ ID NO: 1); #LRP19-3 (SEQ ID NO: 1); #LRP19-10 (SEQ ID NO: 1); #LRP19-12 (SEQ ID NO: 1); #LRP19-13 (SEQ ID NO: 1); #LRP19-1 (SEQ ID NO: 1); #LRP19-4 (SEQ ID NO: 1); #LRP19-5 (SEQ ID NO: 1); #LRP19-6 (SEQ ID NO: 4); #LRP19-14 (SEQ ID NO: 7); #LRP19-11 (SEQ ID NO: 3); #LRP19-8 (SEQ ID NO: 4); #LRP19-2 (SEQ ID NO: 4); #LRP19-9 (SEQ ID NO: 4); #LRP19-7 (SEQ ID NO: 8); #LRP19-15 (SEQ ID NO: 8); #LRP19-16 (SEQ ID NO: 9); #23-c16 (SEQ ID NO: 10); #23-c18 (SEQ ID NO: 11); #23-c21 (SEQ ID NO: 12); #23-c4 (SEQ ID NO: 12); #23-c7 (SEQ ID NO: 13); #23-c9 (SEQ ID NO: 12); #23-1 (SEQ ID NO: 14); #23-2 (SEQ ID NO: 14); #23-3 (SEQ ID NO: 14); #23-4 (SEQ ID NO: 14); #23-5 (SEQ ID NO: 14); #23-6 (SEQ ID NO: 14); #23-7 (SEQ ID NO: 14); #23-8 (SEQ ID NO: 15); #23-9 (SEQ ID NO: 14); #23-10 (SEQ ID NO: 14); #23-11 (SEQ ID NO: 14); #23-12 (SEQ ID NO: 14); #LRP23-1 (SEQ ID NO: 16); #LRP23-12 (SEQ ID NO: 17); #LRP23-4 (SEQ ID NO: 18); #LRP23-9 (SEQ ID NO: 18); #LRP23-7 (SEQ ID NO: 18); #LRP23-3

(SEQ ID NO: 18); #LRP23-8 (SEQ ID NO: 18); #LRP23-6 (SEQ ID NO: 18); #LRP23-2 (SEQ ID NO: 19); #LRP23-11 (SEQ ID NO: 20); #LRP23-14 (SEQ ID NO: 20); #LRP23-15 (SEQ ID NO: 21); #LRP23-5 (SEQ ID NO: 22); #LRP23-10 (SEQ ID NO: 22); and #LRP23-13 (SEQ ID NO: 23).

Figure 4:
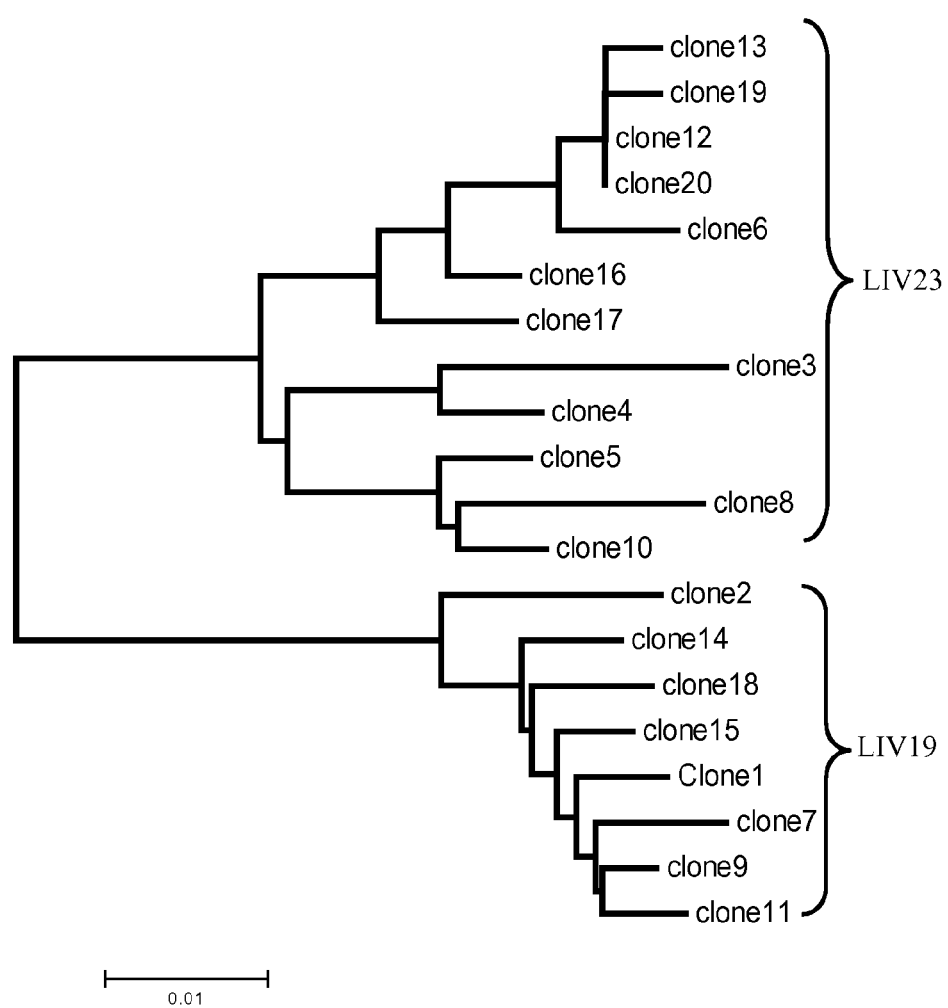

FIG. 4: A representative Neighbor-joining (NJ) tree constructed based on HCV E1 domain of 20 clones derived from 9.1 kb LRP product, which was amplified using mixed serum from samples LIV 19 and LIV23. As expected, all clones are clustered into two groups, LIV19 and LIV23. There is no contradictory clustering for each clone in trees constructed with other seven domains, indicating the lack of LRP-mediated recombination.

DESCRIPTION OF THE TABLES

Table 1. The list of the primers tested during LRP optimization. Also shown are Tm values for all LRP primers as well as the primer sequences used for monitoring HCV cDNA synthesis. Star indicates that primer sequences are involved within putative stem loops [4-6]. Double stars indicate that primers contain restriction sites in their 5' ends. Primer numbering is according to HCV H77 strain (GenBank accession no. NC_004102). All primers were designed with software Eugene version 1.01. Degenerate bases are matched with standard International Union of Pure and Applied Chemistry (IUPAC) codes. Sequences may be identified in the Sequence Listing as follows: QR1 (SEQ ID NO: 24); QR2 (SEQ ID NO: 25); QR268 (SEQ ID NO: 26); QR274 (SEQ ID NO: 27); QR3* (SEQ ID NO: 28); QR4 (SEQ ID NO: 29); QR5 (SEQ ID NO: 30); QR6 (SEQ ID NO: 31); QR7* (SEQ ID NO: 32); Q5BR1 (SEQ ID NO: 33); Q5BR2 (SEQ ID NO: 34); Q5BR3 (SEQ ID NO: 35); QUF1 (SEQ ID NO: 36); QUF2 (SEQ ID NO: 37); QUF3 (SEQ ID NO: 38); QUF4 (SEQ ID NO: 39); QUF5 (SEQ ID NO: 40); WF1 (SEQ ID NO: 41); WF2 (SEQ ID NO: 42); WF3 (SEQ ID NO: 43); WF33 (SEQ ID NO: 44); WF4 (SEQ ID NO: 45); WF5** (SEQ ID NO: 46); WF6 (SEQ ID NO: 47); WF7 (SEQ ID NO: 48); WR1* (SEQ ID NO: 49); WR2* (SEQ ID NO: 50); WR3* (SEQ ID NO: 51); WR4* (SEQ ID NO: 52); WR5 (SEQ ID NO: 53); WTR5 (SEQ ID NO: 54); WR55** (SEQ ID NO: 55); WR6 (SEQ ID NO: 56); WR7 (SEQ ID NO: 57); HCV6 (SEQ ID NO: 58); HCV7 (SEQ ID NO: 59); QUF3 (SEQ ID NO: 60); QUR3 (SEQ ID NO: 61); CoreF2 (SEQ ID NO: 62); CoreR3 (SEQ ID NO: 63); QRAF2 (SEQ ID NO: 64); Q6AR1 (SEQ ID NO: 65); NS3AF2 (SEQ ID NO: 66); NS3AR2 (SEQ ID NO: 67); Q5AF2 (SEQ ID NO: 68); Q5AR2 (SEQ ID NO: 69); Q5BF2 (SEQ ID NO: 70); and Q5BR2 (SEQ ID NO: 71).

Long RT-PCR has been successfully used to amplify large or near full length domains of RNA viruses, including human coronavirus, poliovirus, borna disease virus, porcine reproductive and respiratory syndrome virus, coxsackievirus and hepatitis E virus. It has also been applied to the amplification of cellular RNA derived from such genes as the eurofibromatosis 1 (NF1) and polycystic kidney disease 1 (PKD1) genes. In these studies, a common feature was the availability of good RNA templates in both quantity and quality. In contrast, HCV cannot be easily cultured in vitro although there are recent reports of the establishment of HCV cell culture by using a special HCV genotype 2a strain JFH-1. Clinical samples from patients infected with HCV have a relatively low titer of viral RNA level. In addition, HCV holds a strong structure along with the whole genome. These features may explain the limited success of LRP with HCV. While there have been occasional reports regarding the amplification of near full-length HCV genome, reproducible results were only obtained with the amplification of less than 5 kb fragments in HCV. In contrast, the protocol we have described here has considerable robustness. Besides the two serum samples that we used for optimizing our protocols, we successfully amplified a near full-length HCV genome from an additional 24 patient samples infected with HCV genotype 1a. We identified several critical factors for efficient amplification of a near full-length HCV genome. First, the RT step was conducted by using mixed enzymes, SuperScript III and AMV. SuperScript III is a Moloney Murine Leukemia Virus (M-MLV) with reduced RNase H activity, fully active at temperatures as high as 55° C. Potential RNA secondary structure could be melted at this temperature. However, incubation at 55° C. resulted in decreased sensitivity perhaps due to the partial degradation of the RNA templates. In the optimized protocol, we used 50° C. for the RT reaction. It has been reported that AMV especially favors the reverse transcription of genes with GC-rich domains or strong secondary structure due to its stability at higher temperatures. It is not known how these two enzymes work together, but similar cooperatively has been observed for mixed DNA polymerases in long PCR. In any case, we demonstrated that mixed RT enzymes improve full-length HCV cDNA synthesis in both quality and quantity. Second, not all primers can effectively prime the synthesis of full-length HCV cDNA. In our experiments, only one primer, QR2, (SEQ ID NO: 25) met this requirement, indicating the full-length cDNA synthesis is considerable dependent on the appropriate priming site. To some extent, this observation is consistent with a previous report in which differential priming of RNA templates resulted in obvious differences in both accuracy and reproducibility of RT-PCR. Third, the use of Trnc-21 in PCR steps is recommended. Inclusion of Trnc-21 resulted in automated hot-start PCR amplification. Although there are several techniques available for the initiation of "hot-start" PCR, such as manual control, the use of wax and the addition of antibodies to thermal stable DNA polymerases, none of them is as efficient and convenient as Trnc-21. Finally, the primers for PCR procedures should have appropriate T m values dependent on the annealing/elongation temperatures. Our last optimization step for successful LRP was to raise the annealing/elongation temperature to 72° C. in the second round of PCR, around 5° C. above the primer T m values. The large difference between annealing/elongation temperatures and primer T m values resulted in non-specific amplification while a low annealing/elongation temperature less than 60° C. always abrogated the amplification. There are two salient features for our LRP procedure: the lack of detectable recombination and the preservation of viral diversity, as estimated with samples LIV19 and LIV23. Recombination is generally explained by template switching during PCR, in particularly when the synthesis of complementary strands is stopped prematurely. The lack of detectable recombination in our LRP protocol may be contributed to the reduced cycle numbers (60 cycles versus regular 70 cycles) and Vent DNA polymerase that is included within recombinant *Thermus thermophilus* ("rTth") DNA polymerase, XL and has 3' to 5' exonuclease proof-reading activity. The HVR1 is located at the 5' end of HCV E2 domain and is the most variable region along the entire HCV genome. By comparing genetic parameters for HVR1 quasispecies profiles, our LRP protocol preserves viral heterogeneity, as also reported with a 5 kb HCV amplicon. Furthermore, similar HVR1 quasispecies lineages were obtained with sample LIV19 while sample LIV23 displayed much different HVR1 quasispecies lineages derived from either the 1.38 kb or the 9.1 kb amplicon. By using clones as direct PCR templates, we failed to amplify HVR1 domain by screening 40 clones that had no correct insert confirmed with enzyme digestion after miniculture (data not shown). This excludes the possibility for the loss of potential HVR1 quasispecies lineages during the culture due to the instability of recombinant clones. Thus these results again emphasize the bias of HVR1 quasispecies amplification when using different primer pairs as we previously reported. Still, defective interfering particles (DIP) are another factor to be taken into account. The generation of DIP, natural viral mutants with large deletions in the genome, seems a general phenomenon for all viruses, including HCV. Quasispecies profiles contributed by DIP could be lost in our protocol since only the 9.1 kb fragment was gel-purified prior to cloning. Taken together, the quantitation of viral diversity, if present at a high level within a given sample, is largely underestimated and/or biased by current protocols for PCR amplification and cloning. The technology described here should be applicable to other HCV genotypes as well as other RNA viruses such as GB virus C, HIV and dengue virus. With the amplification and efficient cloning of a near full-length viral genome, it is now possible to study linked mutations at genome-wide scale. Linked mutation is a common strategy exploited by viruses to counter their loss of the fitness resulting from point mutations at immune and/or drug targets. The identification of common patterns of linked mutation is helpful for the improvement of combinational antiviral strategies. In addition, our LRP protocol preserves HCV diversity and has no detectable recombination induced by PCR. These characteristics make it possible to isolate dominant, subdominant, and minor viral variants within a complex virus population, which facilitates the approach of reverse genetics. An initial step in reverse genetics is to construct vectors containing full-length viral genomes, usually assembled by overlapped PCR products that represent viral consensus sequences. However, the consensus sequence is artificial in concept and is not necessarily the dominant viral variant. As a result, replication from infectious clones with consensus viral genome may not occur. This may partially explain why the infectious HCV clone of H77 consensus did not replicate in cell culture while the one with JHF-1 did. In contrast to the existence of multiple HVR1 quasispecies lineages in the patient H77, JHF-1 was derived from a patient with fulminant hepatitis. The immunocompromised status in this patient resulted in an extremely homogenous viral population by cloning analysis of HVR1 domain. In such a situation, consensus viral sequence may be equal to authentic dominant viral variant that makes an "infectious" clone infectious.

Therefore, the invention is drawn to methods and compositions for producing full length DNA from a RNA target genomes comprising (1) a composition and method for extracting target RNA from biological materials, such as for example serum, tissues, cultured cells, etc, (2) a composition and method of using reverse transcriptase for transcribing DNA from full length target RNA, (3) a composition and method of using PCR to amplify the DNA product and (4) a composition and method of cloning DNA.

A composition for RNA extraction is free of carriers for RNA precipitation, such as tRNA and glycogen.

A composition for reverse transcriptase comprises (1) an optimum amount of SuperScript III (Invitrogen) and AMV (Promega) (2) 5× reverse transcription buffer, (3) 0.1 M DTT, and (4) 40 mM dNTPs: 10 mM of each nucleotide dissolved in Tris buffer. Other reverse transcriptase may be substituted for SuperScript III provided a negative Rnase H activity is included. Primers for reverse transcription preferably have a $T_m$ value around 60° C. and away from any stem loop if existed.

A composition for polymerase chain reactions comprises oligonucleotide Trnc-21 and rTth XLpolymerase: (Applied Biosystems). Primers for PCR preferably have a $T_m$ value around 65° C.

A composition for cloning of long RT-PCR product comprises (1) a plasmid of pBR322 origin, kanamycin resistance, MCS with multiple paired restriction enzymes recognizing >7 nucleotides (2) control RNA or DNA template and (3) primers for control templates.

A method for RNA extraction avoids vigorous mixing.

A method for reverse transcriptase includes incubation at 50° C. for 75 minutes, followed by heating to 70° C. for 15 minutes. Additional steps such as preheating of RNA templates are avoided.

A method for PCR comprises cycle parameters of: 94° C. for 1 minute followed by the 10 cycles of 94° C. for 30 seconds, followed by 72° C. for 5~10 minutes (optimum for preservation of long DNA templates), and finally 20 cycles in which the annealing/elongation temperature is reduced to 68°.

Methods for cloning DNA into carriers are well known in the art and generally comprise electroporation, and *E. coli* strain DH10B cells (Invitrogen) as a preferred carrier.

Monitoring HCV cDNA Synthesis

The synthesis of full-length HCV cDNA is a prerequisite for successful LRP. Several groups have performed nested PCR of HCV 5'-UTR after RT step, assuming a positive result as the indicator of full-length HCV cDNA synthesis. However, we found that multiple domains, located within 5'UTR, Core, E2, NS3, NS5a and NS5b, respectively, could be successfully amplified after RT in which RT primers were omitted. This indicated the existence of extensive self-priming during RT presumably induced by HCV RNA secondary structure or oligonucleotides in extracted RNA template. Using the DNA Thermal Cycler 480, the whole procedure for LRP takes at least 2 days. We therefore amplified multiple small fragments (5'UTR, HVR1, NS3, NS5a, NS5b) (Table 1) by using the first round LRP product as the template. After the first round LRP, the effect of self-priming is reduced. The negative amplification of these small fragments indicated the absolute absence of full-length HCV cDNA and thus the second round LRP is not necessary. To test all LRP conditions and parameters alone or in combination, requires hundreds of protocols. Our approach monitors the full-length cDNA synthesis based on first round PCR product. This approach, although not perfect, improves experimental progress significantly.

RNA Extraction

Two RNA extraction procedures, based on either QIAamp Viral RNA Mini Kit (Qiagen) or TRIzol LS reagent (Invitrogen), gave similar LRP results. However, in the latter procedure, the addition of tRNA or glycogen during RNA precipitation, even at low concentration, resulted in the failure of subsequent PCR, suggesting that these carriers had a detrimental role on rTth XL activity.

The optimization of Reverse Transcription can be summarized as follows.

1. SuperScript III outperformed all other reverse transcriptases such as AMV, M-MLV, Expand Reverse Transcriptase, Transcriptor Reverse Transcriptase, SuperScript II and rTth DNA polymerase. Robust LRP results were obtained when running RT with 200 U of SuperScript III at 50° C. for 75 min, followed by inactivation at 70° C. for 15 min. However, using a mixture of SuperScript III (200 U) and AMV (2.5 U), gave LRP results that were much more reproducible, with an increased yield. LRP was not successful using a mixture of RT enzyme and Pfu DNA polymerase, perhaps because the latter had low activity (<30%) in a non-optimized buffer system under RT temperature (50° C.) (Stratagene, personal communication).

2. All additives (except DTT) tested in the RT reaction had an adverse role for LRP. Although these additives have been reported to improve full-length cDNA synthesis, they may be not compatible with SuperScript III or rTth XL DNA polymerase.

3. The selection of RT primers is critical for successful LRP. The most satisfactory and reproducible results were obtained only when using QR2 (SEQ ID NO:25) as the RT primer (Table 1). Interestingly, LRP did not work when replacing QR2 (SEQ ID NO:25) with QR268 (SEQ ID NO: 26) or QR274 (SEQ ID NO: 27), suggesting an appropriate Tm value of RT primers was required. However, LRP failed when modifying other RT primers into a similar Tm value as QR2 (SEQ ID NO:25). In contrast, reproducible amplifications were obtained with other serum samples in which QR2 (SEQ ID NO:25) had one or two nucleotide substitutions. These observations suggest that efficient priming for full-length HCV cDNA synthesis is domain dependent. Additionally, unlike previous reports [30], our LRP is acceptable with QR2 (SEQ ID NO:25) in broad range of concentration from 0.0625 µM to 1 µM.

4. There was no obvious advantage but a reduced sensitivity was observed when purifying RT reaction by using Qiagen spin columns or Dynabeads. Similarly, the use of 7-deaza-2'-deoxyguanosine in RT reaction or RNase H digestion was not advantageous.

PCR

PCR was most successful with rTth DNA polymerase, XL. However, it should be noted that Expand Long Template PCR System and Elongase Enzyme Mix were not thoroughly explored. The former system is the only one known to contain $MgCl_2$, which is also a common component of RT buffers. This makes it potentially promising to reconcile the two buffer systems. Information about additional buffer components is not available, and therefore optimization cannot be performed. There was no improvement and even an adverse effect of other additives (DMSO, betaine and TMA oxalate) and the use of phosphorothioate or loop incorporated primers. However, Trnc-21, an oligonucleotide inhibitor to rTth DNA polymerase, was required for reproducible amplification. The minimum concentration of Trnc-21 is 0.4 µM. We also found no interference to LRP when increasing the concentration up to 1.2 µM. Unlike RT, the requirement for primers in long PCR is less stringent as long as the $T_m$ values of primers are approximately 68° C.

Optimized LRP Protocol

Figure 1:
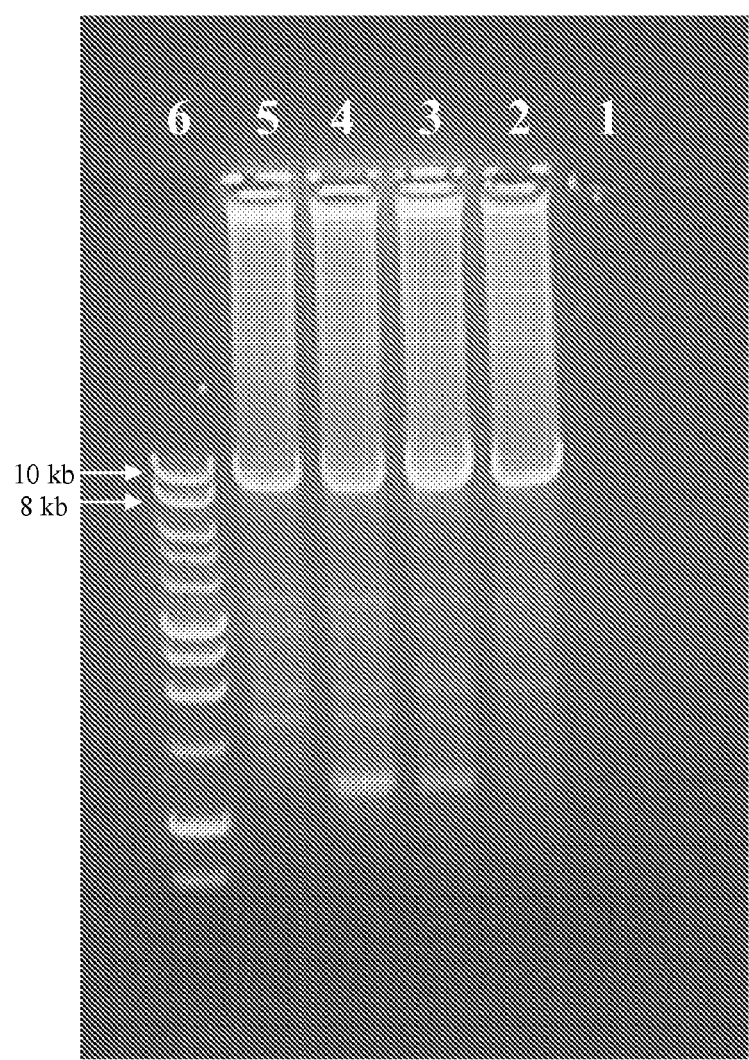
FIG. 1: Amplification of 9.1 kb fragment of HCV genome from serum samples JLR3037 (lanes 2 and 3) and RJ (lanes 4 and 5) by using optimized LRP protocol. The PCR product was electrophoresed on a 0.8% Seakem GTG agarose gel (FMC BioProducts). Lane 1, negative control; Lane 6, 1 kb DNA ladder (Fisher).

RNA was extracted from 280 µl of serum by using QIAamp Viral RNA Mini Kit (Qiagen). 10.6 µl of RNA template was mixed with 9.4 µl of RT matrix consisting of 1× SuperScript III buffer, 10 mM DTT, 1 µM QR2 (reverse primer), 2 mM dNTPs (Invitrogen), 20 U of Rnasein Ribonuclease Inhibitor, 200 U of SuperScript III and 5 U of AMV (Promega). The reaction was performed by incubation at 50° C. for 75 min, followed by heating at 70° C. for 15 min. 5 µl of RT reaction was applied for the first round of PCR that contained 1.25 mM $Mg(OAc)_2$, 1×XL PCR buffer, 2 mM of dNTPs (Invitrogen), 0.4 µM of Trnc-21, 0.4 µM of each primer (WF33 (SEQ ID NO: 44) and QR2 (SEQ ID NO:25)) and 2 U of rTth XL DNA polymerase. Cycle parameters were programmed as 94° C. for 1 min followed by the first 10 cycles of 94° C. for 30 sec and 65° C. for 9 min and final 20 cycles in which the annealing/elongation temperature was reduced to 60° C. for 9 min with a 3 sec autoextension at each cycle. The reaction was ended with 10-min incubation at 72° C. 2 µl of the first round of PCR product was used for the second round amplification with primers WF5 (SEQ ID NO: 46) and WR55 (SEQ ID NO: 55). Cycle parameters were the same as the first round PCR except the annealing/elongation temperature was changed to 72° C. for the first 10 cycles and 68° C. for the last 20 cycles, respectively. Using this protocol, a 9095 by fragment was reproducibly obtained for samples JLR3037 and RJ (FIG. 1).

Robustness and Sensitivity

Figure 2:
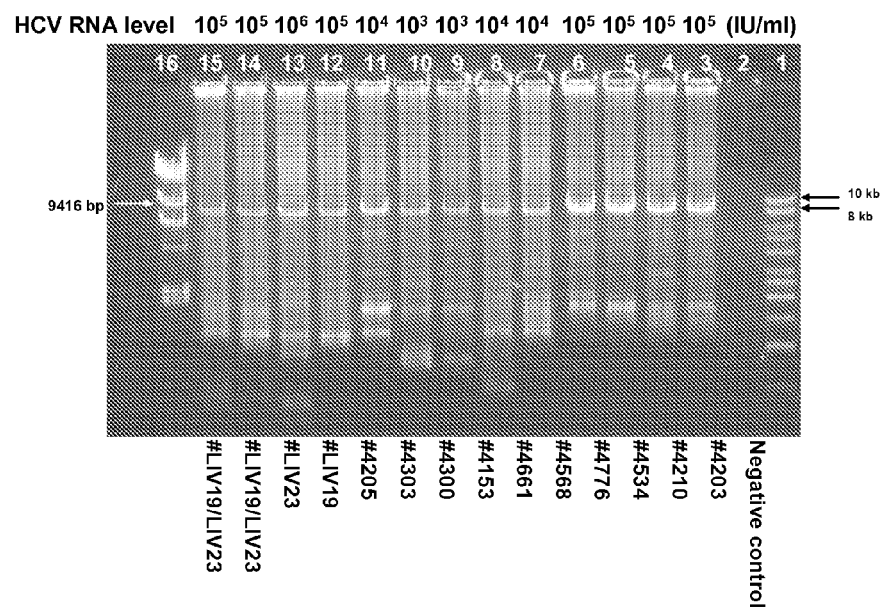
FIG. 2: Amplification of 9.1 kb fragment of HCV genome from additional serum samples with various HCV RNA levels, including samples LIV19 and LIV23. The PCR product was electrophoresed on a 0.8% Seakem GTG agarose gel (FMC BioProducts). Lane 2, negative control; Lane 1, 1 kb DNA ladder (Fisher); Lane 16, Lambda DNA/Hind III markers (Promega).

With the optimized LRP protocol, we tested 24 HCV genotype 1a samples (serum or plasma) with various RNA levels, ranging from $10^3$ to $10^6$ IU/ml. The predicted DNA fragment of 9.1 kb was successfully amplified in all samples, even in those with low HCV RNA levels. A representative result is shown in FIG. 2. These results indicate that our LRP protocol is robust and sensitive. For those samples with HCV RNA levels less than $10^3$ IU/ml, LRP amplification was improved by extracting total RNA from 560 µl of serum instead of 280 µl of serum (data not shown). In our optimized LRP protocol, we used four primers: QR2 (SEQ ID NO:25), WF33 (SEQ ID NO: 44), WF5 (SEQ ID NO: 46) and WR55 (SEQ ID NO: 55). Sequence alignment showed that these primer domains are relatively conservative through most of HCV genotype 1a isolates, especially for 5' end primers WF33 (SEQ ID NO: 44) and WF5 (SEQ ID NO: 46). We also found that one or two nucleotide substitutions within primers QR2 (SEQ ID NO:25) and WR55 (SEQ ID NO: 55) did not abrogate the LRP amplification but resulted in a diminished amount of the amplicon as determined by agarose gel electrophoresis.

Cloning the LRP Product

We encountered unexpected difficulty in cloning the LRP product that is approximately 9.1 kb in length. We repeatedly tried four commercial cloning kits: TOPO XL PCR Cloning Kit, CopyRight Cloning Kit, Clone Smart Blunt Cloning Kit and Gateway Technology with Clonase II. A common problem with these cloning kits was the high background of clones without the insert, which is generally assumed to be as the result of either the toxicity of foreign genes or the instability of recombinant clones. Since pSMART vectors from CopyRight and Clone Smart Blunt Cloning Kits contain multiple terminators that eliminate transcription both into and out of the insert DNA and therefore reduce potential toxicity of the insert, the instability of recombinant clones may be responsible for the high background with false positive clones. We therefore constructed pClone vector that contains pBR origin and restriction sites not found in HCV genome. With this conventional strategy, the LRP product was successfully cloned with DH10B *E. coli* cells but not Stb14 cells. Positive rate for recombinant clones was about 30% which is much higher than previous reports [31, 32]. A 2 ml miniculture yielded approximately 5 µg of recombinant clones, which is a suitable amount for the performance of analysis such as sequencing.

LRP Preserves HCV Quasispecies Diversity

To see if our LRP protocol preserves viral diversity, we evaluated HCV quasispecies based on HVR1 domain derived either from a short amplicon (1.38 kb) or from the LRP product. We sequenced the HVR1 domain from 16 and 15 positive recombinant clones for samples LIV19 and LIV23, respectively. There are generally comparable levels for both genetic complexity and genetic diversity except for a significantly higher genetic complexity at the amino acid level for sample LIV23 (0.829 versus 0.430, p<0.05) (Table 2). Sample LIV19 had a low genetic diversity and similar HVR1 quasispecies lineages were obtained either by short fragment amplification or by LRP (FIG. 3A). However, when comparing HVR1 quasispecies profiles respectively derived from the 1.38 kb and 9.1 kb amplicons in sample LIV23, only one HVR1 lineage was shared by both amplicons (FIG. 3B).

Lack of detection of LRP-mediated recombination LRP was performed using a mixture of equal amounts of serum from samples LIV19 and LIV23. Twenty clones derived from the LRP product were sequenced at 8 domains including 5'UTR, Core, E1, E2, NS2, NS3, NS5a and NS5b. Phylogenetic analysis showed that 8 clones belonged to sample LIV19 and 12 clones were from LIV23. Neighbor-Joining trees constructed with each domain displayed consistent clustering for each clone, suggesting the absence of potential recombination induced by LRP. A representative tree constructed with the HCV E1 domain is shown in FIG. 4. Although we did not sequence 20 clones in full-length, the possibility for recombination is very small, if not excluded, since the 8 domains that we sequenced are evenly scattered along the entire 9.1 kb amplicon.

Materials and Methods

Samples. The LRP optimization was directly conducted with serum samples collected in 2001 from two patients infected with HCV genotype 1a, referred to as JLR3037 and RJ, respectively. A large volume of serum stored at −70° C. was available from these two patients, which allowed repeated and detailed optimization of our LRP protocol. After the optimization, additional serum samples were used for the estimation of sensitivity, robustness and potential recombination (see below). HCV RNA levels were quantitated by bDNA assay (Bayer VERSANT HCV 3.0) immediately prior to the start of this study.

RNA extraction. Total RNA was extracted from serum by using either QIAamp Viral RNA Mini Kit (Qiagen, Valencia, Calif.) or TRIzol LS reagent (Invitrogen, Carlsbad, Calif.) according to the instructions provided. With QIAamp Viral RNA Mini Kit, RNA was extracted from 280 μl of serum and finally eluted into 60 μl of Tris buffer containing 20 U/ml of RNasein Ribonuclease Inhibitor (Promega, Madison, Wis.). In the extraction with TRIzol LS reagent, 250 μl of serum was applied and the RNA pellet was finally dissolved in 20 μl of nuclease-free water containing 20 U/ml of Rnasein Ribonuclease Inhibitor (Promega). Additionally either glycogen (Invitrogen) or transfer RNA (tRNA) (Sigma, St Louis, Mo.) was used for facilitating RNA precipitation. For both methods, vigorous vortexing was avoided to prevent shearing of long RNA templates [7].

Reverse transcription. Since RT is a critical step for successful LRP, we optimized this step as follows. First, we tested multiple RT enzymes alone or in combination, including AMV (Promega), M-MLV (Promega), Expand Reverse Transcriptase (Roche Applied Science, Indianapolis, Ind.), Transcriptor Reverse Transcriptase (Roche Applied Science), SuperScript II (Invitrogen), SuperScript III (Invitrogen) and rTth DNA polymerase (Applied Biosystems, Foster City, Calif.) that shows reverse transcriptase activity in the presence of MnCl2 at elevated temperatures. In some experiments, we mixed a RT enzyme with Pfu DNA polymerase (Stratagene), a similar strategy as used in long PCR, to improve full-length cDNA synthesis [8]. Second, previous studies showed certain chemicals might improve full-length cDNA synthesis in both quantity and quality. In this study, we tried different additives at various concentrations, including DMSO (5-10%) (Sigma), GC-Melt (0.5 M) (BD Biosciences), DTT (5-10 mM), trehalose (0.6 M) (Sigma) [9] and betaine (2 M) (Sigma) [9]. Third, we designed a series of HCV-specific RT primers located at the 3' end of NS5B (Table 1). These primers were tested for efficient priming at different concentrations. Fourth, besides direct application of RT reaction in subsequent PCR, we also tried to purify RT reaction with or without RNase H digestion [11] prior to PCR, by using QIAquick PCR Purification Kit or QIAquick Nucleotide Removal Kit (Qiagen) or Dynabeads KilobaseBINDER Kit (Dynal) in which RT primers were biotinylated at their 5' ends. Finally, we also investigated the role of 7-deaza-2'-deoxyguanosine (Sigma) in the RT reaction that may improve the elongation in GC-rich domains [10].

PCR. All PCR experiments were done with DNA Thermal Cycler 480 (Perkin-Elmer-Cetus, Norwalk, Conn.). The nested PCR strategy and a touchdown protocol were generally applied. At the beginning, we tested several thermostable DNA polymerases for long PCR, such as Expand.

Long Template PCR System (Roche Applied Science) and Elongase Enzyme Mix (Invitrogen). We eventually focused on rTth DNA polymerase, XL (Applied Biosystems, Foster City, Calif.) and most of the optimization experiments were done with this enzyme. The strategy to optimize long PCR was basically similar to what we described for RT step. Multiple additives were first tested, including DMSO, betaine [12, 13] and tetramethylammonium (TMA) oxalate [14]. Next, a series of primers were tested for their efficiency with long PCR (Table 1). Meantime, since one of the mixed polymerases has 3' to 5' exonuclease "proofreading" activity that may degrade primers, we tested phosphorothioate primers to see if the PCR amplification is improved [15-17]. To allow hot-start PCR that may diminish non-specific priming, we adopted two measures, the use of loop incorporated primers [18] and an oligonucleotide, Trnc-21, which specially inhibits DNA polymerase isolated from Thermus thermophilus (Tth pol) at low temperature [19, 20]. Finally, with the DNA Thermal Cycler 480, we empirically fixed denaturing temperature at 94° C. for 30 sec, elongation temperature at 72° C. or 68° C. for 9 min and annealing step for 30 sec. However, the annealing temperature was adjusted depending on the $T_m$ values of the primers (Table 1).

Molecular cloning of HCV envelope domain. HCV displays a typical quasispecies nature shared by most RNA viruses. To understand if our LRP protocol conserves viral diversity, we compared the HCV quasispecies profiles derived from regular RT-PCR and LRP products in two patient samples, LIV19 and LIV23. The viral heterogeneity has been detailed in these two patients in our previous study based on a 1.38 kb amplicon spanning the most hypervariable region 1 (HVR1) of HCV genome [21]. In brief, serum RNA was reverse transcribed with 200 U of M-MLV reverse transcriptase (Promega), followed by nested PCR with Taq DNA polymerase (Applied Biosystems). The PCR product was gel purified by using QIAEX II Gel Extraction Kit (Qiagen) and ligated into the pTOPO-TA cloning vector (Invitrogen). Escherichia coli TOP-10 cells (Invitrogen) were used for transformation and recovery of recombinant clones. Approximately 15 clones for each sample were sequenced with ABI PRISM dye terminator cycle sequencing ready reaction kit using an ABI 373A automated sequencer (Applied Biosystems). Molecular cloning of long RT-PCR product. For cloning the LRP product, we first tried several commercial cloning kits, including TOPO XL PCR Cloning Kit (Invitrogen), Copylight Cloning Kit and Clone Smart Blunt Cloning Kit (Lucigen Corporation, Middleton, Wis.), without success. Next we estimated cloning efficiency of Gateway Technology with Clonase II (Invitrogen). Finally, we returned to a conventional cloning strategy in which the LRP product was digested with two restriction enzymes Pac I and Fse I, followed by ligation into a special plasmid named pClone. The ligation product was electroporated into Stb14 cells or DH10B cells (Invitrogen). The pClone vector was constructed by replacing Pacd-Bam III fragment of pAdTrack-CMV [22] with a ~120 bp fragment that was assembled to include rare restriction enzymes not found in the HCV genome based on an analysis of 13 full-length HCV genotype 1a isolates. Positive recombinant clones were identified by either the digestion or partial sequencing of both ends of the insert.

Estimation of PCR-mediated recombination. PCR may induce a homologous recombination [23-25]. The rate of recombination is dependent on the protocol used. After the optimization of our long RT-PCR, we estimated the potential recombination related to this protocol. In doing so, sera from samples LIV19 and LIV23 were mixed in equal amounts, followed by the same procedures of RNA extraction, RT, long PCR and cloning. Approximately 20 positive recombinant clones were sequenced at 8 domains located within 5'UTR, Core, E1, E2, NS2, NS3, NS5a and NS5b regions, respectively. Recombination would be indicated for a given clone if conflicting clusterings were noted in phylogenetic trees constructed with 1 of the 8 domains that we sequenced.

Genetic analysis. All sequences were aligned with Clustal W (version 1.74) [26]. Sequence editing and multiple sequence comparisons were performed with matched programs in the Wisconsin GCG package (Oxford Molecular Group, Inc., version 10.0). The mean genetic distance (d), the number of synonymous substitutions per synonymous site (dS) and the number of nonsynonymous substitutions per nonsynonymous site (dN) were calculated with the Kimura 2-parameter method (all sites) [27] in the Molecular Evolutionary Genetics Analysis software package (MEGA, version 3.0) [28]. All phylogenetic trees were constructed using the NeighborJoining method [29] with a bootstrap test implanted in MEGA. The genetic complexity at both nucleotide and amino acid level was evaluated respectively for samples LIV19 and LIV 23 by calculating normalized entropy (Sn): Sn=S/lnN, where N is the total number of clones; S=Σi(pilnpi), where pi is the frequency of each clone in the viral quasispecies population.

Statistical tests. Student' t-test was used to analyze differences between mean values for genetic parameters when data were normally distributed. Nonparametric tests were used to evaluate samples for which normal distributions were not present.

REFERENCES

Applicants make no statement, inferred or direct, regarding the status of the following references as prior art. Applicants reserve the right to challenge the veracity of any statements made in these references, which are incorporated herein by reference.

1. W. M. Barnes, PCR amplification of up to 35-kb DNA with high fidelity and high yield from lambda bacteriophage templates, Proc. Natl. Acad. Sci. USA. 91(1994) 2216-2220.
2. S. Cheng, C. Fockler, W. M. Barnes, R. Higuchi, Effective amplification of long targets from cloned inserts and human genomic DNA, Proc. Natl. Acad. Sci. USA. 91 (1994) 5695-5699.
3. K. M. Chumakov, Reverse transcriptase can inhibit PCR and stimulate primer-dimer formation, PCR Meth. Appl. 4 (1994) 62-64.
4. A. Tuplin, J. Wood, D. J. Evans, A. H. Patel, P. Simmonds, Thermodynamic and phylogenetic prediction of RNA secondary structures in the coding region of hepatitis C virus, RNA 8(2002) 824-841.
5. A. Tuplin, D. J. Evans, P. Simmonds, Detailed mapping of RNA secondary structures in core and NS5B-encoding region sequences of hepatitis C virus by RNase cleavage and novel bioinformatic prediction methods, J. Gen. Virol. 85 (2004) 3037-3047. 6. P. Simmonds, A. Tuplin, D. J. Evans, Detection of genome-scale ordered RNA structure (GORS) in genomes of positive-stranded RNA viruses: Implications for virus evolution and host persistence, RNA 10(2004) 1337-1351.
7. L. Lu, T. Nakano, G. A. Smallwood, T. G. Heffron, B. H. Robertson, C. H. Hagedorn, A refined long RT-PCR technique to amplify complete viral RNA genome sequences from clinical samples: Application to a novel hepatitis C virus variant of genotype 6, J. Virol. Methods 126 (2005) 139-148.
8. P. R. Hawkins, P. Jin, G. K. Fu, Full-length cDNA synthesis for long-distance RT-PCR of large mRNA transcripts, Biotechniques 34 (2003) 768-770.
9. A. N. Spiess, R. Ivell, A highly efficient method for long-chain cDNA synthesis using trehalose and betaine, Anal. Biochem. 301 (2002) 168-174.
10. L. McConlogue, M. A. Brow, M. A. Innis, Structure-independent DNA amplification by PCR using 7-deaza-2'-deoxyguanosine, Nucleic Acids Res. 16 (1988) 9869.
11. S. K. Polumuri, A. Ruknudin, D. H. Schulze, RNase H and its effects on PCR, Biotechniques 32 (2002) 1224-1225.
12. W. Henke, K. Herdel, K. Jung, D. Schnorr, S. A. Loening, Betaine improves the PCR amplification of GC-rich DNA sequences, Nucleic Acids Res. 25 (1997) 3957-3958.
13. P. N. Hengen, Optimizing multiplex and LA-PCR with betaine, Trends Biochem. Sci. 22 (1997) 225-226.
14. M. Kovarova, P. Draber, New specificity and yield enhancer of polymerase chain reactions, Nucleic Acids Res. 28 (2000) E70.
15. A. Skerra, Phosphorothioate primers improve the amplification of DNA sequences by DNA polymerases with proofreading activity, Nucleic Acids Res. 20 (1992) 3551-3554.
16. C. M. de Noronha, J. I Mullins, Amplimers with 3'-terminal phosphorothioate linkages resist degradation by vent polymerase and reduce Taq polymerase mispriming, PCR Meth. Appl. 2 (1992) 131-136.
17. D. Di Giusto, G. C. King, Single base extension (SBE) with proofreading polymerases and phosphorothioate primers: improved fidelity in single-substrate assays, Nucleic Acids Res. 31 (2003) e7.
18. M. Ailenberg, M. Silverman, Controlled hot start and improved specificity in carrying out PCR utilizing touch-up and loop incorporated primers (TULIPS), Biotechniques 29 (2000) 1018-1020.
19. C. Dang, S. D. Jayasena, Oligonucleotide inhibitors of Taq DNA polymerase facilitate detection of low copy number targets by PCR, J. Mol. Biol. 64 (1996) 268-278.
20. Y. Lin, S. D. Jayasena, Inhibition of multiple thermostable DNA polymerases by a heterodimeric aptamer, J. Mol. Biol. 271 (1997) 100-111.
21. T. J. Chambers, X. Fan, D. A. Droll, E. Hembrador, T. Slater, M. W. Nickells, L. B. Dustin, A. M. DiBisceglie, Quasispecies heterogeneity within the E1/E2 region as a pretreatment variable during pegylated interferon therapy of chronic hepatitis C virus infection, J. Virol. 79 (2005) 3071-3083.

22. T. C. He, S. Zhou, L. T. da Costa, J. Yu, K. W. Kinzler, B. A. Vogelstein, A simplified system for generating recombinant adenoviruses, Proc. Natl. Acad. Sci. USA. 95(1998) 2509-2514.

23. M. S. Judo, A. B. Wedel, C. Wilson, Stimulation and suppression of PCR-mediated recombination, Nucleic Acids Res. 26 (1998) 1819-1825.

24. S. Shafikhani, Factors affecting PCR-mediated recombination, Environ. Microbiol. 4 (2002) 482-486.

25. G. Fang, G. Zhu, H. Burger, J. S. Keithly, B. Weiser, Minimizing DNA recombination during long RT-PCR, J. Virol. Methods 76 (1998) 139-148.

26. D. G. Higgins, P. M. Sharp, CLUSTAL: a package for performing multiple sequence alignment on a microcomputer, Gene 73 (1988) 237-244.

27. M. Kimura, A simple method for estimating evolutionary rates of base substitutions through comparative studies of nucleotide sequences. J. Mol. Evol. 16 (1980) 111-120.

28. S. Kumar, K. Tamura, M. Nei, MEGA3: Integrated Software for Molecular Evolutionary Genetics Analysis and Sequence Alignment, Brief. Bioinform. 5 (2004) 150-163.

29. N. Saitou, M. Nei, The neighbor-joining method: a new method for reconstructing phylogenetic trees, Mol. Biol. Evol. 4 (1987) 406-425.

30. V. Thiel, A. Rashtchian, J. Herold, D. M. Schuster, N. Guan, S. G. Siddell, Effective amplification of 20-kb DNA by reverse transcription PCR, Anal. Biochem. 252 (1997) 62-70.

31. A. A. Kolykhalov, E. V. Agapov, K. J. Blight, K. Mihalik, S. M. Feinstone, C. M. Rice, Transmission of hepatitis C by intrahepatic inoculation with transcribed RNA, Science 277 (1996) 570-574.

32. M. Yanagi, R. H. Purcell, S. U. Emerson, J. Bukh, Transcripts from a single full-length cDNA clone of hepatitis C virus are infectious when directly transfected into the liver of a chimpanzee, Proc. Natl. Acad. Sci. USA 94 (1997) 8738-8743.

33. K. Rispeter, M. Lu, S. Lechner, A. Zibert, M. Roggendorf, Cloning and characterization of a complete open reading frame of the hepatitis C virus genome in only two cDNA fragments, J. Gen. Virol. 78 (1997) 2751-2759.

34. H. J. Boot, R. M. Schepp, F. J. van Nunen, T. G. Kimman, Rapid RT-PCR amplification of full-length poliovirus genomes allows rapid discrimination between wild-type and recombinant vaccine-derived polioviruses, J. Virol. Methods 116 (2004) 35-43.

35. Y. Shoya, T. Kobayashi, T. Koda, P. K. Lai, H. Tanaka, T. Koyama, K. Ikuta, M. Kakinuma, M. Kishi, Amplification of a full-length Borna disease virus (BDV) cDNA from total RNA of cells persistently infected with BDV, Microbiol. Immunol. 41 (1997) 481-486.

36. H. S. Nielsen, T. Storgaard, M. B. Oleksiewicz, Analysis of ORF 1 in European porcine reproductive and respiratory syndrome virus by long RT-PCR and restriction fragment length polymorphism (RFLP) analysis, Vet. Microbiol. 76 (2000) 221-228.

37. T. A. Martino, R. Tellier, M. Petric, D. M. Irwin, A. Afshar, P. P. Liu, The complete consensus sequence of coxsackievirus B6 and generation of infectious clones by long RT-PCR, Virus Res. 64 (1999) 77-86.

38. S. Jameel, M. Zafrullah, Y. K. Chawla, J. B. Dilawari, Reevaluation of a North India isolate of hepatitis E virus based on the full-length genomic sequence obtained following long RT-PCR, Virus Res. 86 (2002) 53-58.

39. J. M. Martinez, H. H. Breidenbach, R. Cawthon, Long RT-PCR of the entire 8.5-kb NF1 open reading frame and mutation detection on agarose gels, Genome Res. 6 (1996) 58-66.

40. W. Thongnoppakhun, P. Wilairat, K. Vareesangthip, P. T. Yenchitsomanus, Long RT PCR Amplification of the entire coding sequence of the polycystic kidney disease 1 (PKD1) gene, Biotechniques 26 (1999) 126-132.

41. J. Zhong, P. Gastaminza, G. Cheng, S. Kapadia, T. Kato, D. R. Burton, S. F. Wieland, S. L. Uprichard, T. Wakita, F. V. Chisari, Robust hepatitis C virus infection in vitro, Proc. Natl. Acad. Sci. 102 (2005) 9294-9299.

42. T. Wakita, T. Pietschmann, T. Kato, T. Date, M. Miyamoto, Z. Zhao, K. Murthy, A. Habermann, H. Kräusslich, M. Mizokami, R. Bartenschlager, T. J. Liang, Production of infectious hepatitis C virus in tissue culture from a cloned viral genome, Nature Med. Published online: 12 Jun. 2005.

43. B. D. Lindenbach, M. J. Evans, A. J. Syder, B. Wölk, T. L. Tellinghuisen, C. C. Liu, T. Maruyama, R. O. Hynes, D. R. Burton, J. A. McKeating, C. M. Rice, Complete Replication of Hepatitis C Virus in Cell Culture, Science, Published online 9 Jun. 2005.

44. L. F. Wang, M. Radkowski, H. Vargas, J. Rakela, T. Laskus T, Amplification and fusion of long fragments of hepatitis C virus genome. J. Virol. Methods 68 (1997) 217-223.

45. R. Tellier, J. Bukh, S. U. Emerson, R. H. Miller, R. H. Purcell, Long PCR and its application to hepatitis viruses: amplification of hepatitis A, hepatitis B, and hepatitis C virus genomes, J. Clin. Microbiol. 34 (1996) 3085-3091.

46. Z. Liu, D. M. Netski, Q. Mao, O. Laeyendecker, J. R. Ticehurst, X. H. Wang, D. L. Thomas, S. C. Ray, Accurate representation of the hepatitis C virus quasispecies in 5.2 kilobase amplicons, J. Clin. Microbiol. 42(2004) 4223-4229.

47. P. Sheehy, M. Scallan, E. Kenny-Walsh, F. Shanahan, L. J. Fanning, A strategy for obtaining near full-length HCV cDNA clones (assemblicons) by assembly PCR, J. Virol. Methods 123(2005) 115-124.

48. J. Zhang, C. D. Byrne, Differential priming of RNA templates during cDNA synthesis markedly affects both accuracy and reproducibility of quantitative competitive reverse transcriptase PCR, Biochem. J. 337 (1999) 231-241.

49. X. Fan, A. C. Lyra, D. Tan, Y. Xu, A. M. Di Bisceglie, Differential amplification of hypervariable region 1 of hepatitis C virus by partially mismatched primers, Biochem. Biophys. Res. Commun. 284(2001) 694-697.

50. C. R. M. Bangham and T. B. L. Kirkwood, Defective interfering particles and virus evolution, Trends in Microbiol. 1 (1993) 260-264.

51. A. M. Prince, T. Huima-Byron, T. S. Parker and D. M. Levine, Visualization of hepatitis C virons and putative defective interfering particles isolated from low-density lipoproteins, J. Viral Hepatitis 3(1996) 11-17.

52. P. Farci, A. Shimoda, A Coiana, G. Diaz, G. Peddis, J. C. Melpolder, A. Strazzera, D. Y. Chien, S. J. Munoz, A. Balestrieri, R. H. Purcell, H. J. Alter, The outcome of acute hepatitis C predicted by the evolution of the viral quasispecies, Science 288 (2000) 339 344.

53. T. Kato, A. Furusaka, M. Miyamoto, T. Date, K. Yasui, J. Hiramoto, K. Nagayama, T. Tanaka, T. Wakita, Sequence analysis of hepatitis C virus isolated from a fulminant hepatitis patient, J. Med. Virol. 64 (2001) 334-339.

What is claimed:

1. A method of making a polydeoxynucleotide comprising the steps of
   (a) obtaining a ribonucleotide from a sample and placing it in a buffer containing deoxynucleotide triphosphates,
   (b) adding to the ribonucleotide a mixture of at least two reverse transcriptases comprising at least one reverse transcriptase with reduced RNase H activity,
   (c) adding to the ribonucleotide and mixture of at least two reverse transcriptases, a reverse transcription oligonucleotide primer, as set forth in SEQ ID NO: 25, to obtain a reverse transcription cocktail,
   (d) heating the reverse transcription cocktail to 50° C. for at least about 75 minutes followed by heating to 70° C., to produce a complementary polydeoxynucleotide ("cDNA"), followed by,
   (e) addition of
      (i) a first deoxynucleotide polymerase oligonucleotide primer,
      (ii) a second deoxynucleotide polymerase oligonucleotide primer,
      (iii) a Trnc-21 molecule, and
      (iv) a deoxynucleotide polymerase to the reverse transcription cocktail plus cDNA mixture, to obtain a polymerase chain reaction ("PCR") cocktail,
   (f) heating the PCR cocktail to about 94° C. for about one (1) minute,
   (g) followed by 10 cycles of 94° C. for 30 seconds, followed by 72° C. for 5-10 minutes, and then
   (h) 20 cycles in which the annealing/elongation temperature is reduced to 60° C.

2. The method of claim 1 wherein the at least two reverse transcriptases comprise Moloney Murine Leukemia Virus (M-MLV) with reduced RNase H activity and Avian Myeloblastosis Virus ("AMV") reverse transcriptase.

3. The method of claim 1 wherein the deoxynucleotide polymerase is a recombinant *Thermus thermophilus* ("rTth") DNA polymerase.

4. The method of claim 1, wherein the at least two reverse transcriptases comprise Moloney Murine Leukemia Virus (M-MLV) with reduced RNase H activity and Avian Myeloblastosis Virus ("AMV") reverse transcriptase, the deoxynucleotide polymerase is a recombinant *Thermus thermophilus* ("rTth") DNA polymerase, the reverse transcription oligonucleotide primer consists of the sequence set forth in SEQ ID NO: 25, the first deoxynucleotide polymerase oligonucleotide primer consists of the sequence set forth in SEQ ID NO: 25, and the second deoxynucleotide polymerase oligonucleotide primer consists of the sequence set forth in SEQ ID NO: 44.

5. A method of producing a hepatitis C virus polynucleotide comprising,
   (a) extracting polyribonucleic acid ("RNA") from serum,
   (b) mixing the RNA with a reverse transcription ("RT") matrix consisting 1× SUPERSCRIPT III® buffer, 10 mM DTT, 1 μM primer set forth in SEQ ID NO: 25, 2 mM dNTPs, 20 U of RNasein Ribonuclease Inhibitor, 200 U of Moloney Murine Leukemia Virus (M-MLV) with reduced RNase H activity and 5 U of Avian Myeloblastosis Virus ("AMV") reverse transcriptase,
   (c) incubating at 50° C. for 75 min, followed by heating at 70° C. for 15 min, to form a reverse transcription reaction mixture,
   (d) mixing a portion of the reverse transcription reaction mixture to a polymerase chain reaction ("PCR") buffer containing 1.25 mM Mg(OAc)$_2$, 1×XL PCR buffer, 2 mM of dNTPs, 0.4 μM of Trnc-21, 0.4 μM of SEQ ID NO: 44, 0.4 μM of SEQ ID NO: 25, and 2 U of rTth XL DNA polymerase, to form a first PCR mixture,
   (e) subjecting the first PCR mixture to thermal cycles of 94° C. for 1 min followed by the first 10 cycles of 94° C. for 30 sec and 65° C. for 9 m in and final 20 cycles in which the annealing/elongation temperature is 60° C. for 9 min with a 3 sec autoextension at each cycle, followed by a single 10-min incubation at 72° C. to form a first PCR product,
   (f) mixing a portion of the first PCR product with primers as set forth in SEQ ID NO: 46 and SEQ ID NO: 55 in the PCR buffer as in (d) to form a second PCR mixture,
   (g) subjecting the second PCR mixture to thermal cycles of 94° C. for 1 min followed by the first 10 cycles of 72° C. for 30 sec and 65° C. for 9 min and final 20 cycles in which the annealing/elongation temperature is 68° C. for 9 min with a 3 sec auto extension at each cycle, followed by a single 10-min incubation at 72° C.

6. A method of making a polydeoxynucleotide comprising the steps of
   (a) obtaining a ribonucleotide from a sample and placing it in a buffer containing deoxynucleotide triphosphates,
   (b) adding to the ribonucleotide a mixture of at least two reverse transcriptases comprising at least one reverse transcriptase with reduced RNase H activity,
   (c) adding to the ribonucleotide and mixture of at least two reverse transcriptases, a reverse transcription oligonucleotide primer, as set forth in SEQ ID NO: 25 with one or two nucleotide substitutions, to obtain a reverse transcription cocktail,
   (d) heating the reverse transcription cocktail to 50° C. for at least about 75 minutes followed by heating to 70° C., to produce a complementary polydeoxynucleotide ("cDNA"), followed by,
   (e) addition of
      (i) a first deoxynucleotide polymerase oligonucleotide primer,
      (ii) a second deoxynucleotide polymerase oligonucleotide primer,
      (iii) a Trnc-21 molecule, and
      (iv) a deoxynucleotide polymerase to the reverse transcription cocktail plus cDNA mixture, to obtain a polymerase chain reaction ("PCR") cocktail,
   (f) heating the PCR cocktail to about 94° C. for about one minute,
   (g) followed by 10 cycles of 94° C. for 30 seconds, followed by 72° C. for 5-10 minutes, and
   (h) 20 cycles in which the annealing/elongation temperature is reduced to 60° C.

* * * * *